US012721680B2

(12) United States Patent
Chen et al.

(10) Patent No.: US 12,721,680 B2
(45) Date of Patent: Sep. 1, 2026

(54) METHOD AND APPARATUS FOR EVALUATING AORTIC DISSECTION SURGERY, ELECTRONIC DEVICE, AND STORAGE MEDIUM

(71) Applicant: Beijing Institute of Technology, Beijing (CN)

(72) Inventors: Duanduan Chen, Beijing (CN); Yilun Zhang, Beijing (CN); Huanming Xu, Beijing (CN); Zhenfeng Li, Beijing (CN); Yuqian Mei, Beijing (CN); Yue Shi, Beijing (CN)

(73) Assignee: Beijing Institute of Technology, Beijing (CN)

(*) Notice: Subject to any disclaimer, the term of this patent is extended or adjusted under 35 U.S.C. 154(b) by 1158 days.

(21) Appl. No.: 17/769,885

(22) PCT Filed: Oct. 29, 2020

(86) PCT No.: PCT/CN2020/124825
§ 371 (c)(1),
(2) Date: Apr. 18, 2022

(87) PCT Pub. No.: WO2021/083275
PCT Pub. Date: May 6, 2021

(65) Prior Publication Data

US 2022/0296304 A1 Sep. 22, 2022

(30) Foreign Application Priority Data

Oct. 31, 2019 (CN) ......................... 201911057269.2

(51) Int. Cl.

| | |
|---|---|
| ***A61B 34/10*** | (2016.01) |
| ***G16H 10/60*** | (2018.01) |
| *A61B 17/00* | (2006.01) |

(52) U.S. Cl.
CPC ............ *A61B 34/10* (2016.02); *G16H 10/60* (2018.01); *A61B 2017/00292* (2013.01); *A61B 2034/104* (2016.02)

(58) Field of Classification Search
CPC .... A61B 2017/00292; A61B 2034/102; A61B 2034/104; A61B 2034/105; A61B 34/10; G16H 10/60
See application file for complete search history.

(56) References Cited

U.S. PATENT DOCUMENTS

2018/0125583 A1* 5/2018 Redel .................... A61B 6/504
2019/0105008 A1 4/2019 Dehghan et al.
(Continued)

FOREIGN PATENT DOCUMENTS

CN 102680324 A 9/2012
CN 103917164 A 7/2014
(Continued)

*Primary Examiner* — Mark D Remaly
(74) *Attorney, Agent, or Firm* — Mark C. Johnson; Johnson |Dalal

(57) ABSTRACT

A method and apparatus for evaluating aortic dissection surgery, an electronic device, and a storage medium are provided. The method comprises: obtaining a preoperative aortic model of a patient; simulating aortic dissection surgery on the basis of a virtual stent technology and the preoperative aortic model to obtain a postoperative aortic model; obtaining displacement amount of the same blood vessel node between the preoperative aortic model and the preoperative aortic model; and evaluating a surgical risk degree of the patient on the basis of the displacement amount. The occurrence probability of postoperative complications is related to the displacement amount.

6 Claims, 4 Drawing Sheets

(56) References Cited

U.S. PATENT DOCUMENTS

| | | | | |
|---|---|---|---|---|
| 2019/0209243 | A1* | 7/2019 | Schuurmann .......... | G16H 30/40 |
| 2019/0357981 | A1* | 11/2019 | Mortier .................. | A61B 34/10 |
| 2020/0118688 | A1* | 4/2020 | Pasta ...................... | G16B 20/00 |

FOREIGN PATENT DOCUMENTS

| | | | |
|---|---|---|---|
| CN | 106539622 | A | 3/2017 |
| CN | 108764221 | | 6/2018 |
| CN | 105243686 | A | 8/2018 |
| CN | 105249954 | A | 10/2018 |
| CN | 108764221 | A | 11/2018 |
| CN | 108969097 | A | 12/2018 |
| CN | 109003278 | | 12/2018 |
| CN | 109003278 | A | 12/2018 |
| CN | 109064559 | A | 12/2018 |
| CN | 109700527 | | 3/2019 |
| CN | 109700527 | A | 5/2019 |
| CN | 109907732 | A | 6/2019 |
| CN | 109925056 | A | 6/2019 |
| CN | 109934913 | A | 6/2019 |
| CN | 110392914 | A | 10/2019 |
| CN | 110742689 | A | 2/2020 |

* cited by examiner

METHOD AND APPARATUS FOR EVALUATING AORTIC DISSECTION SURGERY, ELECTRONIC DEVICE, AND STORAGE MEDIUM

CROSS-REFERENCE TO RELATED APPLICATIONS

The present disclosure claims priority to Chinese Patent Application No. 201911057269.2, entitled "Method and Apparatus for Evaluating Aortic Dissection Surgery, Electronic Device, and Storage Medium" and filed with the Chinese Patent Office on Oct. 31, 2019, the entire contents of which are incorporated herein by reference.

TECHNICAL FIELD

The present disclosure relates to the field of medical treatment technology, and in particular to a method and an apparatus for evaluating an aortic dissection surgery, an electronic device, and a storage medium.

BACKGROUND ART

Arteries, as the main blood vessels in the body, are directly subjected to the impact of huge blood flow and the pressure of beating from the heart, and the situation of tearing of the intima of the arteries easily occurs, which leads to the occurrence of aortic dissection (AD). Aortic dissection is an arterial disease with a rapid onset and a high mortality rate. For patients who are not treated in time, the mortality rate is high. The anatomical structure of the aortic wall tissue is divided into intima, media (tunica media) and adventitia. The pathological characteristics of dissection are manifested as that the intima ruptures, and the blood enters the artery media from the tear, to make the media stripped from the adventitia to form another lumen (false lumen) separate from the original artery (true lumen) and extending distally and/or proximally along the artery.

In the prior art, since the postoperative condition of a patient with aortic dissection can usually only be evaluated after an actual aortic dissection surgery is performed, the doctor cannot timely make a medical plan according to the postoperative condition of the patient.

SUMMARY

In view of this, the embodiments of the present disclosure are intended to provide a method and an apparatus for evaluating an aortic dissection surgery, an electronic device, and a storage medium, to evaluate the patient's risk degree of the aortic dissection surgery before surgery, so as to facilitate doctors making a reasonable medical plan timely to improve the survival rate of the patient.

In a first aspect, an embodiment of the present disclosure provides a method for evaluating an aortic dissection surgery, the method including: obtaining a preoperative aortic model of a patient; simulating an aortic dissection surgery on the basis of a virtual stent technology and the preoperative aortic model to obtain a postoperative aortic model; obtaining a displacement amount of a same vessel node between the preoperative aortic model and the postoperative aortic model with the same vessel node located in the preoperative aortic model and the postoperative aortic model respectively; and evaluating a surgical risk degree of the patient on the basis of the displacement amount.

In the above implementation process, the postoperative aortic model is obtained by simulating the aortic dissection surgery on the basis of the virtual stent technology and the preoperative aortic model; then, the displacement amount of the same vessel node between the preoperative aortic model and the postoperative aortic model with the same vessel node located in the preoperative aortic model and the postoperative aortic model respectively; and finally, the surgical risk degree of the patient is evaluated on the basis of the displacement amount. Since the occurrence probability of postoperative complications is related to the displacement amount, the surgical risk degree can be evaluated in this way before the surgery, so as to facilitate doctors making a reasonable medical plan timely according to the evaluation result to improve the survival rate of the patient.

Based on the first aspect, in a possible design, the evaluating the surgical risk degree of the patient on the basis of the displacement amount includes: comparing the displacement amount with a preset displacement amount, and evaluating the surgical risk degree of the patient according to the comparison result.

In the above implementation process, the displacement amount is compared with the preset displacement amount, and then the surgical risk degree of the patient is evaluated according to the comparison result. In this way, the surgical risk degree can be more reasonably evaluated before surgery.

Based on the first aspect, in a possible design, subsequent to the step of obtaining the displacement amount of the same vessel node between the preoperative aortic model and the postoperative aortic model with the same vessel node located in the preoperative aortic model and the postoperative aortic model respectively, the method further includes: determining, based on a spatial position of the same vessel node in the postoperative aortic model and the displacement amount, a type of a complication that may occur in the patient after surgery.

In the above implementation process, based on the spatial position of the same vessel node in the postoperative aortic model and the displacement amount, the type of the complication that may occur in the patient after surgery is determined. Since the type of the complication that may occur in the patient after surgery is related to the displacement amount and the spatial position of the vessel node in the postoperative aortic model, the type of the complication that may occur in the patient after surgery can be determined in this way before surgery, so that the doctors can timely determine a name of the complication based on the type of the complication.

Based on the first aspect, in a possible design, subsequent to the step of obtaining the postoperative aortic model, the method further includes: transecting the postoperative aortic model in a direction perpendicular to a centerline of the postoperative aortic model to obtain a plurality of cross sections; simulating blood flow in the postoperative aortic model at a predetermined blood flow rate and detecting a pressure intensity difference between a true lumen and a false lumen in each of the cross sections; and evaluating postoperative recovery of the patient based on the pressure intensity difference.

In the above implementation process, the blood flow is simulated in the simulated postoperative aortic model at a predetermined blood flow rate, and then the postoperative recovery is evaluated using the pressure intensity difference between the true lumen and the false lumen in each cross section in the postoperative aortic model. Since the postoperative recovery of the patient is related to the factor of pressure intensity difference between the true lumen and the false lumen, the accuracy of the evaluation result can be improved in this way.

Based on the first aspect, in a possible design, the evaluating postoperative recovery of the patient based on the pressure intensity difference includes: obtaining, when determining that there is a cross section with a pressure intensity difference of zero, a position of the cross section in the postoperative aortic model; and evaluating postoperative recovery of the patient on the basis of the position of the cross section.

In the above implementation process, when it is determined that there is a cross section with the pressure intensity difference of zero in the postoperative aortic model, the position of the cross section is determined, and then the postoperative recovery of the patient is evaluated based on the position of the cross section before surgery. Since the position of the cross section with the pressure intensity difference of zero is related to the recovery of the patient, the accuracy of the evaluation result can be further improved in this way.

Based on the first aspect, in a possible design, the detecting a pressure intensity difference between a true lumen and a false lumen in each of the cross sections includes: detecting multiple sets of pressure intensity difference data between the true lumen and the false lumen in each of the cross sections; and determining, as the pressure intensity difference, an average value of the multiple sets of pressure intensity difference data.

In the above implementation process, for each cross section, the average value of the multiple sets of pressure intensity difference data corresponding to the cross section is determined as the pressure intensity difference, and in this way, the postoperative recovery of the patient can be evaluated more accurately.

In a second aspect, an embodiment of the present disclosure provides a method for evaluating an aortic dissection surgery, the method including: obtaining a preoperative aortic model of a patient; simulating an aortic dissection surgery on the basis of a virtual stent technology and the preoperative aortic model to obtain a postoperative aortic model; transecting the postoperative aortic model in a direction perpendicular to a centerline of the postoperative aortic model to obtain a plurality of cross sections; simulating blood flow in the postoperative aortic model at a predetermined blood flow rate and detecting a pressure intensity difference between a true lumen and a false lumen in each of the cross sections; and evaluating a postoperative condition of the patient based on the pressure intensity difference.

In the above implementation process, the aortic dissection surgery is simulated on the basis of the virtual stent technology and the preoperative aortic model of the patient, the blood flow is simulated in the simulated postoperative aortic model at a predetermined blood flow rate, and then the postoperative condition is evaluated using the pressure intensity difference between the true lumen and the false lumen in each cross section in the postoperative aortic model. Since the postoperative condition of the patient is related to the factor of pressure intensity difference between the true lumen and the false lumen, the postoperative condition of the patient can be evaluated in this way.

In a third aspect, an embodiment of the present disclosure provides an apparatus for evaluating an aortic dissection surgery, the apparatus including: a preoperative model obtaining unit configured to obtain a preoperative aortic model of a patient; a postoperative model obtaining unit configured to simulate an aortic dissection surgery on the basis of a virtual stent technology and the preoperative aortic model to obtain a postoperative aortic model; a displacement amount obtaining unit configured to obtain a displacement amount of a same vessel node between the preoperative aortic model and the postoperative aortic model with the same vessel node located in the preoperative aortic model and the postoperative aortic model respectively; and a first evaluating unit, configured to evaluate a surgical risk degree of the patient on the basis of the displacement amount.

Based on the third aspect, in a possible design, the first evaluating unit is configured to compare the displacement amount with a preset displacement amount and evaluate the surgical risk degree of the patient according to the comparison result.

Based on the third aspect, in a possible design, the apparatus further includes a complication type determining unit, configured to determine, based on a spatial position of the same vessel node in the postoperative aortic model and the displacement amount, a type of a complication that may occur in the patient after surgery.

Based on the third aspect, in a possible design, the apparatus further includes: a cross section obtaining unit configured to transect the postoperative aortic model in a direction perpendicular to a centerline of the postoperative aortic model to obtain a plurality of cross sections; a pressure intensity difference obtaining unit configured to simulate blood flow in the postoperative aortic model at a predetermined blood flow rate and detect a pressure intensity difference between a true lumen and a false lumen in each of the cross sections; and a second evaluating unit configured to evaluate postoperative recovery of the patient based on the pressure intensity difference.

Based on the third aspect, in a possible design, the second evaluating unit is further configured to obtain, when determining that there is a cross section with the pressure intensity difference of zero, a position of the cross section in the postoperative aortic model; and evaluate the postoperative recovery of the patient on the basis of the position of the cross section.

Based on the third aspect, in a possible design, the pressure intensity difference obtaining unit is further configured to detect multiple sets of pressure intensity difference data between the true lumen and the false lumen in each of the cross sections; and determine as the pressure intensity difference an average value of the multiple sets of pressure intensity difference data.

In a fourth aspect, an embodiment of the present disclosure provides an apparatus for evaluating an aortic dissection surgery, the apparatus including: a first model obtaining unit configured to obtain a preoperative aortic model of a patient; a second model obtaining unit configured to simulate an aortic dissection surgery on the basis of a virtual stent technology and the preoperative aortic model to obtain a postoperative aortic model; a cross section obtaining unit configured to transect the postoperative aortic model in a direction perpendicular to a centerline of the postoperative aortic model to obtain a plurality of cross sections; a pressure intensity difference detecting unit configured to simulate blood flow in the postoperative aortic model at a predetermined blood flow rate and detect a pressure intensity difference between a true lumen and a false lumen in each of the cross sections; and a third evaluating unit configured to evaluate a postoperative condition of the patient based on the pressure intensity difference.

In a fifth aspect, an embodiment of the present disclosure provides an electronic device, including a processor and a memory connected to the processor, the memory having computer programs stored therein, wherein when the computer programs are executed by the processor, the electronic device is enabled to perform the method according to the first aspect and the second aspect.

In a sixth aspect, an embodiment of the present disclosure provides a storage medium having computer programs stored therein, wherein the computer programs, when running on a computer, enables the computer to execute the method according to the first aspect and the second aspect.

Other features and advantages of the present disclosure will be described hereinafter, and partly become obvious from the description or be understood by implementing the embodiments of the present disclosure. The objectives and other advantages of the present disclosure may be implemented and attained by the structure particularly pointed out in the drafted description, claims and drawings.

BRIEF DESCRIPTION OF DRAWINGS

For clear description of the technical solutions in the embodiments of the present disclosure, drawings to be used in the embodiments will be briefly introduced below. It should be understood that the following drawings merely illustrate some embodiments of the present disclosure and therefore should not be construed as limiting the scope of the present disclosure. Those skilled in the art also could obtain other drawings based on these drawings without doing creative labor.

DETAILED DESCRIPTION OF EMBODIMENTS

Figure 1:
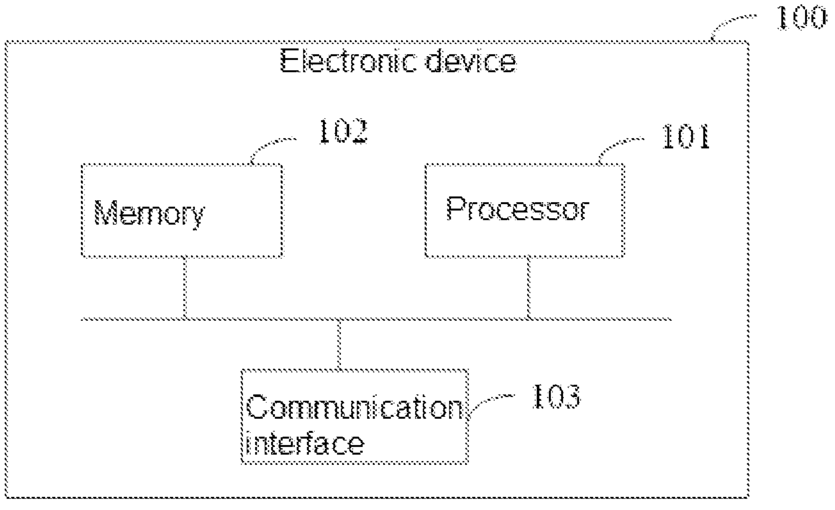
FIG. 1 is a schematic structural diagram of an electronic device according to an embodiment of the present disclosure.

The technical solutions in the embodiments of the present disclosure will be described below with reference to the accompanying drawings in the embodiments of the present disclosure.

It should be noted that similar reference numerals and letters denote similar items in the following accompanying drawings, and therefore, once an item is defined in a drawing, it is not necessary to further define and explain it in the following accompanying drawings. In addition, in the description of the present disclosure, the terms "first" and/or "second" and the like are only used to distinguish the description, and cannot be understood as indicating or implying importance in relativity.

Different patients with aortic dissection may have different surgical risks after aortic dissection surgery. Therefore, it is desired to evaluate the surgical risk degree of a patient before surgery, so as to facilitate doctors making a reasonable medical plan timely according to the evaluation result to improve the survival rate of the patient.

An embodiment of the present disclosure provides a schematic structural diagram of an electronic device 100. As shown in FIG. 1, the electronic device 100 may be a personal computer (PC), a tablet computer, a smart phone, and/or a personal digital assistant (PDA) and the like.

The electronic device 100 may include a memory 102, a processor 101, a communication interface 103, and a communication bus which is configured to enable connection and communication of these components.

The memory 102 is configured to store various types of data such as the patient's preoperative aortic model, postoperative aortic model, displacement amount, and evaluation result, a preoperative aortic Computed Tomography angiography (CTA) image of the patient with aortic dissection, and computing program instructions corresponding to the method and apparatus for evaluating an aortic dissection surgery according to the embodiments of the present disclosure. In the above, the memory 102 can be, but is not limited to, a Random Access Memory (RAM), a Read Only Memory (ROM), a Programmable Read-Only Memory (PROM), an Erasable Programmable Read-Only Memory (EPROM), an Electric Erasable Programmable Read-Only Memory (EEPROM), and the like.

When configured to read and run computer program instructions stored in the memory, the processor 101 executes the steps of the method for evaluating an aortic dissection surgery according to the embodiments of the present disclosure, so as to obtain the patient's preoperative aortic model or preoperative CTA image from the memory, and simulate an aortic dissection surgery on the basis of a virtual stent technology and the preoperative aortic model to obtain a postoperative aortic model, and then compute a displacement amount of a same vessel node between the preoperative aortic model and the postoperative aortic model with the same vessel node located in the preoperative aortic model and the postoperative aortic model respectively, and finally evaluate a surgical risk degree of the patient on the basis of the displacement amount to obtain an evaluation result. The processor 102 is further configured to store the evaluation result, the displacement amount and the postoperative aortic model in the memory 102.

Here, the processor 101 may be an integrated circuit chip with a signal processing capability. The above-mentioned processor 101 may be a general-purpose processor, including a Central Processing Unit (CPU), a Network Processor (NP), and the like; it may also be a digital signal processor (DSP), an application-specific integrated circuit (ASIC), a field programmable gate array (FPGA) or other programmable logic devices, discrete gate or transistor logic devices and/or discrete hardware components. It can implement or execute the methods, steps, and logical block diagrams disclosed in the embodiments of the present disclosure. The general-purpose processor may be a microprocessor or the processor may also be any conventional processor or the like.

The communication interface 103 can use any device such as a transceiver to send the evaluation result to a user terminal in communication with the electronic device 100 for display.

Figure 2:
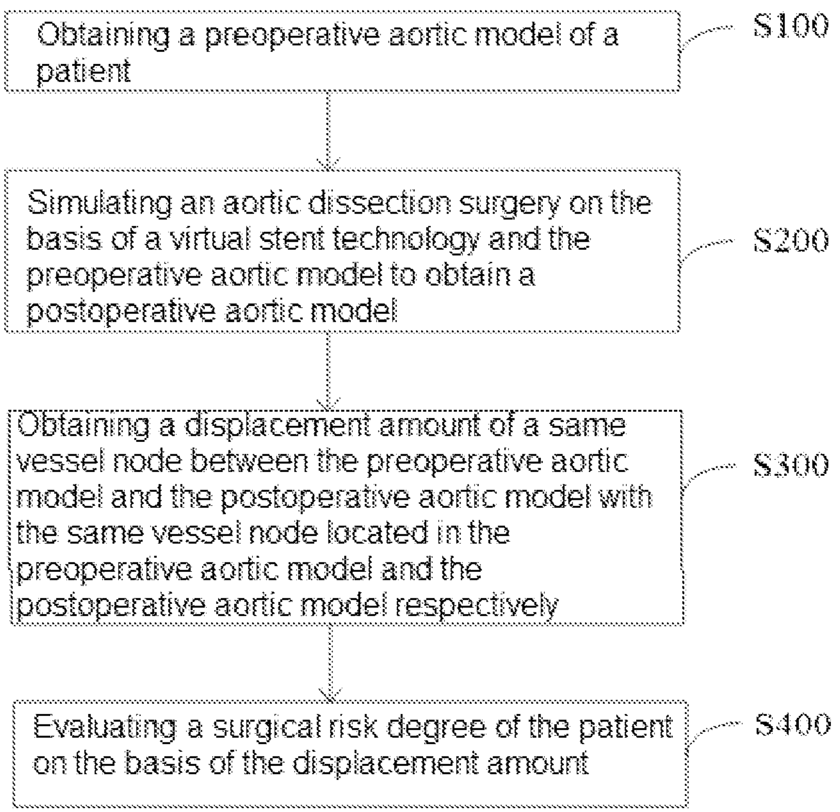
FIG. 2 is a flowchart of a method for evaluating an aortic dissection surgery according to an embodiment of the present disclosure.

Referring to FIG. 2, FIG. 2 is a flowchart of a method for evaluating an aortic dissection surgery according to an embodiment of the present disclosure. The method is applied to the electronic device 100 as shown in FIG. 1. The method comprises S100, S200, S300, and S400.

In S100, a preoperative aortic model of a patient is obtained.

In S200, an aortic dissection surgery is simulated on the basis of a virtual stent technology and the preoperative aortic model to obtain a postoperative aortic model.

In S300, a displacement amount of a same vessel node between the preoperative aortic model and the postoperative aortic model is obtained, with the same vessel node located in the preoperative aortic model and the postoperative aortic model respectively.

In S400, a surgical risk degree of the patient is evaluated on the basis of the displacement amount.

The flow shown in FIG. 2 will be described in detail below.

In S100, a preoperative aortic model of a patient is obtained.

In a possible implementation, S100 may be implemented as follows: obtaining an arterial CTA image of a patient with aortic dissection, wherein in this embodiment, the CTA image refers to an arterial CTA image of a patient with type B aortic dissection, and in other embodiments, it may be other types of arterial CTA images; determining the geometric shape of the arterial vessel based on an image processing technology, and then performing three-dimensional reconstruction of the arterial vessel based on the geometric shape to obtain the preoperative aortic model.

Since the aortic model obtained by the three-dimensional reconstruction is a continuous model and cannot be directly applied to computing of a computer, the continuous preoperative aortic model can be subject to grid processing to obtain the spatial position of each grid point on the artery, that is, obtain the spatial position of each vessel node on the artery. Here, the grid processing is specifically implemented by: performing discretization on the preoperative aortic model by using triangular grids to obtain the aortic model of triangular grids, and then obtaining a spatial position of each vertex on the triangular grids.

Because the triangular grids are not smooth enough, the boundary of the artery is not processed well. Therefore, in the process of obtaining the spatial position of each vessel node on the artery, as another implementation, by utilizing that there is a topological duality relationship between triangular grids and simplex grids in the space, that is, the centroid of each triangular grid is the vertex corresponding to the simplex grid, and the vertices corresponding to the simplex grids are connected in pairs, and then the aortic model of triangular grids is converted into an aortic model of simplex grids to improve the boundary processing effect of the artery and obtain the spatial position of each simplex grid vertex, that is, the spatial position of each vessel node.

Since how to establish a preoperative aortic model is well known to those skilled in the art, it will not be described in detail here.

In S200, an aortic dissection surgery is simulated on the basis of a virtual stent technology and the preoperative aortic model to obtain a postoperative aortic model.

In a possible implementation, S200 may be implemented as follows. Since the virtual stent technology can simulate the aortic dissection surgery, it is required to obtain the centerline of the preoperative aortic model and/or the diameter of the arterial vessel in the arterial vessel model, as well as actual stent parameters, wherein the stent parameters include the length and/or diameter of a stent, and the like. Taking the centerline as a center, a 3D virtual stent model is generated. Here, the virtual stent model is placed inside the aortic model, and then the virtual stent model is subjected to grid processing by using the above-mentioned grid processing method, to obtain a virtual stent model of simplex grids, and then, the spatial position of each simplex grid vertex in the virtual stent model, i.e., the spatial position of each stent node, is obtained.

In order to determine the end time of the simulation of aortic dissection surgery to obtain the postoperative aortic model corresponding to the end time, taking the contact between the virtual stent and the artery as a critical point, the expansion process of the virtual stent in the artery is divided into two stages.

In the first stage, the virtual stent does not touch the arterial vessel wall during the expansion process. In this stage, each stent node is only subjected to an internal expansion force. The second stage starts when the virtual stent contacts the arterial vessel and ends when the expansion of the stent ends, wherein in this stage, the stent nodes in contact with the arterial vessel will not only be subjected to the internal expansion force, but also receive an inward reverse force of the arterial vessel wall, that is, the external compression force.

For each stent node, the values of the external compression force and the internal expansion force that the stent node suffers are computed. When the values of the internal expansion force and the external compression force that the stent node suffers are in balance, the simulation of the aortic dissection surgery comes to the end. At the end of the simulation of the surgery, the postoperative aortic model corresponding to the end time is obtained, and based on the postoperative aortic model, the spatial position of each vessel node is obtained. In the above, the balance between the internal expansion force value and the external compression force value means that the difference therebetween is less than a first preset difference, and the internal expansion force value and the compression pressure value are not required to be completely equal. The first preset difference is set according to actual needs, and can be set to 1 Newton, or can also be set to 0.5 Newton or 2 Newtons, or the like.

As another possible implementation, S200 includes: simulating the aortic dissection surgery on the basis of a finite element method and the preoperative aortic model to obtain a postoperative aortic model. Since the use of the finite element method to simulate the aortic dissection surgery is the prior art, it is not repeated here.

In S300, a displacement amount of a same vessel node between the preoperative aortic model and the postoperative aortic model is obtained, with the same vessel node located in the preoperative aortic model and the postoperative aortic model respectively.

After the preoperative aortic model and the postoperative aortic model of the patient are obtained, for the same vessel node in the preoperative aortic model and the postoperative aortic model, a first spatial position of the vessel node on the preoperative aortic model and a second spatial position of the vessel node on the postoperative aortic model are obtained and a distance between the first spatial position and the second spatial position is computed, and then the displacement amount of the same vessel node between the preoperative aortic model and the postoperative aortic model is obtained, with the same vessel node located in the preoperative aortic model and the postoperative aortic model respectively.

As an embodiment, subsequent to S300, the method further includes:

determining, based on a spatial position of the same vessel node in the postoperative aortic model and the displacement amount, a type of a complication that may occur in the patient after surgery.

After the displacement amount corresponding to each vessel node is obtained, a vessel node A with a largest displacement amount is determined and then the displacement amount corresponding to the vessel node is compared with a preset displacement amount. When the displacement amount corresponding to the vessel node A is greater than the preset displacement amount, the type of a complication that may occur in the patient after surgery is determined on the basis of the spatial position of the vessel node A in the postoperative aortic model. Here, the preset displacement amount may be determined according to multiple sets of actual vessel displacement amount measurement data of the patient with aortic dissection before and after surgery. In this embodiment, the preset displacement amount is 15 mm. In other embodiments, the preset displacement amount may be 13 mm, 14 mm, or 16 mm. When it is determined that the spatial position of the vessel node A in the postoperative aortic model is relatively close to the patient's heart, it is determined that the patient is prone to reverse tear near this vessel node after surgery; and when it is determined that the spatial position of the vessel node A in the postoperative aortic model is relatively far from the patient's heart, it is determined that the patient is prone to internal leak near this vessel node after surgery.

In S400, a surgical risk degree of the patient is evaluated on the basis of the displacement amount.

As an embodiment, S400 includes:

comparing the displacement amount with a preset displacement amount and evaluating the surgical risk degree of the patient according to the comparison result.

The displacement amount is compared with the preset displacement amount, and the probability that the patient may have a risk of complications, for example, occurrence of internal leak and/or reverse tear, or the like, after surgery can be determined according to the comparison result. In this embodiment, the preset displacement amount is 16 mm, and in other embodiments, the preset displacement amount may be 15 mm or 17 mm, or the like. When the displacement amount is less than the preset displacement amount, it is determined that the probability that the patient has complication(s) is relatively small; when the displacement amount is 0 to 2 mm greater than the preset displacement amount, it is determined that the probability that the patient has complication(s) is moderate; when the displacement amount is greater than the preset displacement amount by 2.1 mm, it is determined that the probability that the patient has complication(s) is high. As an embodiment, S400 includes: evaluating a surgical risk degree of the patient on the basis of the displacement amount.

Since mechanical parameters are closely related to the remodeling of the artery, the postoperative recovery of the patient is related to a pressure intensity difference between the true lumen and the false lumen. The true lumen and the false lumen may be squeezed or expanded under action of pressures, when the pressures of the true lumen and the false lumen of the cross section of the artery are different. Therefore, as an embodiment, subsequent to S200, the method further includes: S210, S220 and S230.

In S210, the postoperative aortic model is transected in a direction perpendicular to a centerline of the postoperative aortic model to obtain a plurality of cross sections.

In the above, during the transection, equidistant transection can be carried out to obtain multiple cross sections. It can be understood that the distance between any two adjacent cross sections is equal. Here, the above-mentioned perpendicular is not limited to absolutely perpendicular, for example may refer to any value from 80 degrees to 90 degrees.

Certainly, as an embodiment, the artery in the aortic model can also be arbitrarily transected in a direction perpendicular to the centerline, and the distance between any two adjacent cross sections can be unequal.

Optionally, the centerline of the postoperative aortic model may be the centerline of the true lumen in the postoperative aortic model.

Certainly, the centerline of the postoperative aortic model may also be the centerline of the artery formed by the true lumen and the false lumen.

In S220, blood flow is simulated in the postoperative aortic model at a predetermined blood flow rate and a pressure intensity difference between a true lumen and a false lumen in each of the cross sections is detected.

As an embodiment, in order to obtain the pressure intensity difference between the true lumen and the false lumen on each cross section, blood flow is first simulated in the postoperative aortic model at a predetermined blood flow rate, the pressure on the true lumen and the pressure on the false lumen in each cross section are then detected during blood flow, and then the cross-sectional area of the true lumen and the cross-sectional area of the false lumen on this cross section are obtained, and true lumen pressure intensity and false lumen pressure intensity on each cross section are then obtained using a computational formula of pressure intensity, pressure and cross-sectional area. Here, the predetermined blood flow rate may be a blood flow rate determined according to multiple sets of actual blood flow rate data of the patient after surgery.

In the above, in this embodiment, for each cross section, only one set of pressure intensity data (i.e., one true lumen pressure intensity value and one false intensity pressure intensity value) may be obtained.

Certainly, as another embodiment, when blood is flowing, the pressure intensity difference between the true lumen and the false lumen on each of the cross sections can be detected multiple times to obtain multiple sets of pressure intensity difference data, and then, the multiple sets of pressure intensity difference data are averaged to obtain the pressure intensity difference, so as to improve the accuracy of the evaluation result. The "multiple sets" here may be two or more sets and it will not be specifically limited in the present disclosure.

In S230, the postoperative recovery of the patient is evaluated on the basis of the pressure intensity difference.

As an embodiment, for the postoperative aortic model, when the pressure intensity difference corresponding to each cross section is obtained, it is determined whether there is a cross section with the pressure intensity difference of zero. When it is determined that there is a cross section with the pressure intensity difference of zero, it indicates that there is a cross section of which the false lumen pressure intensity is higher than the true lumen pressure intensity on the artery of the patient after surgery, the postoperative recovery of the patient is general, the remodeling effect of the true lumen is not good, and the blood flow in the false lumen is still high.

When it is determined that there is no cross section with the pressure intensity difference of zero, it indicates that the patient recovers well in terms of morphology after surgery (i.e., the true lumen volume of the patient after surgery is much larger than the false lumen volume); and the true lumen pressure intensity is higher than the false lumen pressure intensity for each cross section on the artery, which indicates that the patient has a good recovery after surgery, the remodeling effect of the true lumen is obvious, and the blood flow in the false lumen is significantly reduced, and it is determined that the patient has a good recovery after surgery.

As an embodiment, S230 includes:

obtaining, when determining that there is a cross section with the pressure intensity difference of zero, the position of the cross section in the postoperative aortic model. In the above, in this embodiment, an intersection of the centerline intersecting the cross section is determined as the position of the cross section in the postoperative aortic model; in other embodiments, the position of any point on the cross section is determined as the position of the cross section in the postoperative aortic model; and evaluating the postoperative recovery of the patient on the basis of the position of the cross section.

When it is determined that the distance between the position of the cross section and an iliac tear is smaller than a first preset distance value, it indicates that a situation where the false lumen pressure intensity is greater than the true lumen pressure intensity only occurs at the position on the artery away from the heart, and it is determined that the patient has a slightly worse morphological remodeling effect than that in the situation where there is no zero-point difference, but has less total flow into the false lumen after surgery than that of the patient having no zero-point pressure intensity difference, which is more conducive to complete thrombosis of the false lumen, and it is thus determined that the patient has good postoperative recovery.

When it is determined that the position of the cross section is close to an abdominal tear, it is determined that the patient has a poor morphological remodeling effect, and the false lumen still maintains a relatively smooth blood flow, which is not conducive to thrombosis.

Figure 3:
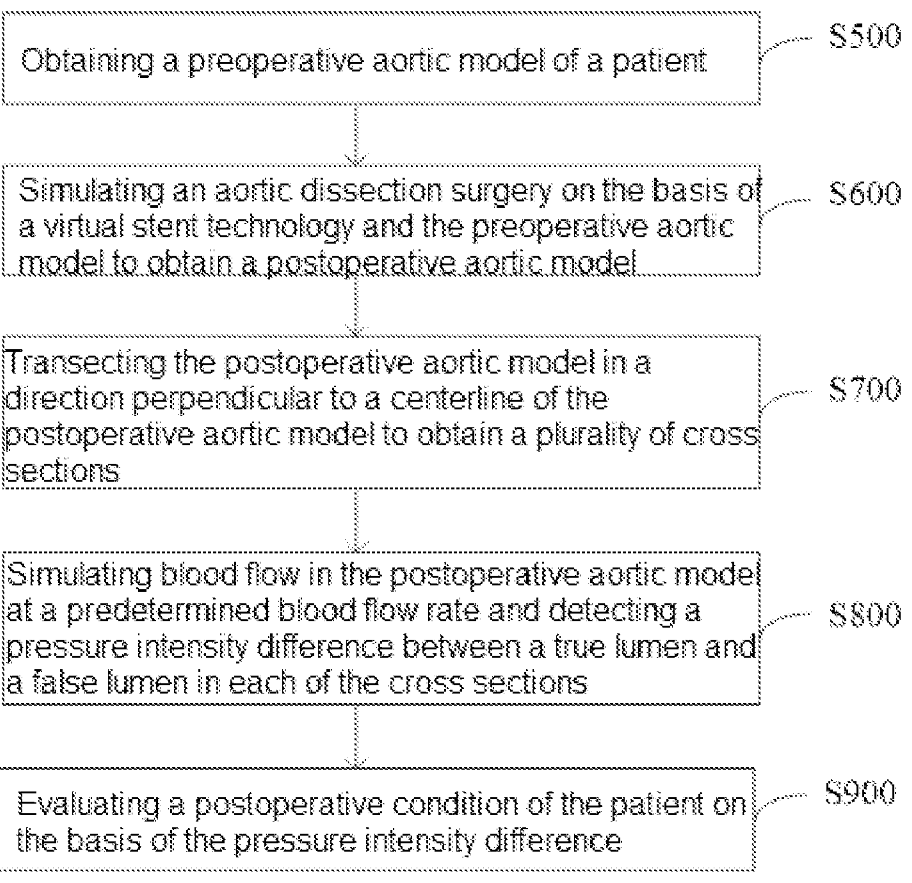
FIG. 3 is a flowchart of another method for evaluating an aortic dissection surgery according to an embodiment of the present disclosure.

Referring to FIG. 3, FIG. 3 is a flowchart of another method for evaluating an aortic dissection surgery according to an embodiment of the present disclosure. The method includes S500, S600, S700, S800 and S900.

In S500, a preoperative aortic model of a patient is obtained.

In S600, an aortic dissection surgery is simulated on the basis of a virtual stent technology and the preoperative aortic model to obtain a postoperative aortic model.

In S700, the postoperative aortic model is transected in a direction perpendicular to a centerline of the postoperative aortic model to obtain a plurality of cross sections.

In S800, blood flow is simulated in the postoperative aortic model at a predetermined blood flow rate and a pressure intensity difference between a true lumen and a false lumen in each of the cross sections is detected.

In S900, a postoperative condition of the patient is evaluated on the basis of the pressure intensity difference.

As an embodiment, S900 includes:

obtaining, when determining that there is a cross section with a pressure intensity difference of zero, a position of the cross section in the postoperative aortic model; and evaluating a postoperative condition of the patient on the basis of the position of the cross section.

As an embodiment, S800 includes:

detecting multiple sets of pressure intensity difference data between a true lumen and a false lumen in each of the cross sections; and determining, as the pressure intensity difference, an average value of the multiple sets of pressure intensity difference data.

For the description of the method for evaluating an aortic dissection surgery according to this embodiment of the present disclosure, reference is made to the description of the embodiment shown in FIG. 2, and it will not be repeated here.

Figure 4:
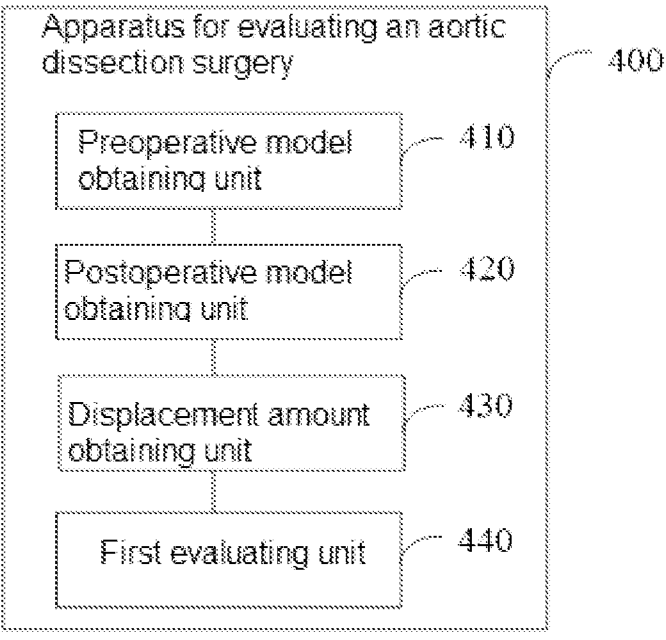
FIG. 4 is a schematic structural diagram of an apparatus for evaluating an aortic dissection surgery according to an embodiment of the present disclosure.

Referring to FIG. 4, FIG. 4 is a structural block diagram of an apparatus 400 for evaluating an aortic dissection surgery according to an embodiment of the present disclosure. The structural block diagram shown in FIG. 4 will be described below, and the shown device includes:

a preoperative model obtaining unit 410 configured to obtain a preoperative aortic model of a patient;

a postoperative model obtaining unit 420 configured to simulate an aortic dissection surgery on the basis of a virtual stent technology and the preoperative aortic model to obtain a postoperative aortic model;

a displacement amount obtaining unit 430 configured to obtain a displacement amount of a same vessel node between the preoperative aortic model and the postoperative aortic model with the same vessel node located in the preoperative aortic model and the postoperative aortic model respectively; and a first evaluating unit 440 configured to evaluate a surgical risk degree of the patient on the basis of the displacement amount.

As an embodiment, the first evaluating unit 440 is configured to compare the displacement amount with a preset displacement amount and evaluate the surgical risk degree of the patient according to the comparison result.

As an embodiment, the apparatus further includes a complication type determining unit, configured to determine, based on a spatial position of the same vessel node in the postoperative aortic model and the displacement amount, a type of a complication that may occur in the patient after surgery.

As an embodiment, the apparatus further includes: a cross section obtaining unit configured to transect the postoperative aortic model in a direction perpendicular to a centerline of the postoperative aortic model to obtain a plurality of cross sections; a pressure intensity difference obtaining unit configured to simulate blood flow in the postoperative aortic model at a predetermined blood flow rate and detect a pressure intensity difference between a true lumen and a false lumen in each of the cross sections; and a second evaluating unit configured to evaluate postoperative recovery of the patient based on the pressure intensity difference.

As an embodiment, the second evaluating unit is further configured to obtain, when determining that there is a cross section with the pressure intensity difference of zero, a position of the cross section in the postoperative aortic model; and evaluate the postoperative recovery of the patient on the basis of the position of the cross section.

As an embodiment, the pressure intensity difference obtaining unit is further configured to detect multiple sets of pressure intensity difference data between the true lumen and the false lumen in each of the cross sections; and determine, as the pressure intensity difference, an average value of the multiple sets of pressure intensity difference data.

For the process of implementing the respective functions of the functional units of this embodiment, reference is made to the content described in the embodiment shown in FIG. 2 above, and details are not repeated here.

Figure 5:
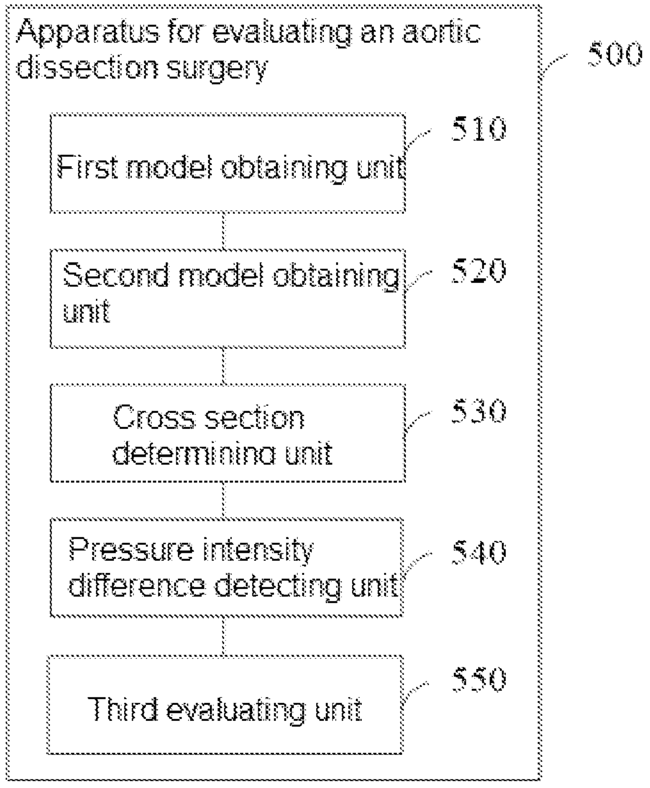
FIG. 5 is a schematic structural diagram of another apparatus for evaluating an aortic dissection surgery according to an embodiment of the present disclosure.

Referring to FIG. 5, FIG. 5 is a structural block diagram of another apparatus 500 for evaluating an aortic dissection surgery according to an embodiment of the present disclosure. The structural block diagram shown in FIG. 5 will be described below, and the shown device includes:

a first model obtaining unit 510 configured to obtain a preoperative aortic model of a patient;

a second model obtaining unit 520 configured to simulate an aortic dissection surgery on the basis of a virtual stent technology and the preoperative aortic model to obtain a postoperative aortic model;

a cross section determining unit 530 configured to transect the postoperative aortic model in a direction perpendicular to a centerline of the postoperative aortic model to obtain a plurality of cross sections;

a pressure intensity difference detecting unit 540 configured to simulate blood flow in the postoperative aortic model at a predetermined blood flow rate and detect a pressure intensity difference between a true lumen and a false lumen in each of the cross sections; and a third evaluating unit 550 configured to evaluate a postoperative condition of the patient on the basis of the pressure intensity difference.

For the process of implementing the respective functions of the functional units of this embodiment, reference is made to the content described in the embodiments shown in FIG. 2 and FIG. 3 above, and details are not repeated here.

In addition, an embodiment of the present disclosure further provides a storage medium having computer programs stored therein, and the computer programs, when running on a computer, enables the computer to execute the method for evaluating an aortic dissection surgery according to any of the embodiments of the present disclosure.

In summary, various embodiments of the present disclosure provide a method and an apparatus for evaluating an aortic dissection surgery, an electronic device and a storage medium. The method includes: obtaining a preoperative aortic model of a patient; simulating an aortic dissection surgery on the basis of a virtual stent technology and the preoperative aortic model to obtain a postoperative aortic model; obtaining a displacement amount of a same vessel node between the preoperative aortic model and the postoperative aortic model with the same vessel node located in the preoperative aortic model and the postoperative aortic model respectively; and evaluating a surgical risk degree of the patient on the basis of the displacement amount. Since the occurrence probability of postoperative complications is related to the displacement amount, the surgical risk degree can be evaluated before surgery in this way, so as to facilitate doctors making a reasonable medical plan timely according to the evaluation result to improve the survival rate of the patient.

In the embodiments of the present disclosure, it should be understood that the disclosed apparatus and method may also be implemented in other ways. The apparatus embodiments described above are merely illustrative, for example, the flowcharts and block diagrams in the accompanying drawings illustrate the possibly implemented architecture, function, and operation of apparatuses, methods and computer program products according to various embodiments of the present disclosure. In this regard, each of the blocks in the flowcharts or block diagrams may represent a part of a module, program segment or code; the part of a module, program segment or code includes one or more executable instructions configured to implement the specified logic functions. It should also be noted that, in some alternative implementations, the functions noted in the block may occur out of the order noted in the figures. For example, two blocks in succession may, in fact, be executed substantially concurrently, or the blocks may sometimes be executed in the reverse order, depending upon the function involved. It should also be noted that each block in the block diagrams and/or flow charts, as well as the combinations of blocks in the block diagrams and/or flow charts, may be implemented with a dedicated hardware-based apparatus that performs a specified function or action, or may be implemented with a combination of dedicated hardware and computer instructions.

In addition, the functional modules in various embodiments of the present disclosure can be combined together to form an independent part, or each module can exist separately, or two or more modules can be integrated to form an independent part.

What is claimed is:

1. A method for evaluating an aortic dissection surgery, comprising steps of:

obtaining a preoperative aortic model of a patient;

simulating an aortic dissection surgery based on a virtual stent technology and the preoperative aortic model to obtain a postoperative aortic model;

obtaining a displacement amount of a same vessel node between the preoperative aortic model and the postoperative aortic model with the same vessel node located in the preoperative aortic model and the postoperative aortic model respectively; and evaluating a surgical risk degree of the patient based on the displacement amount, subsequent to the step of obtaining the preoperative aortic model, the method further comprising steps of:

transecting the postoperative aortic model in a direction perpendicular to a centerline of the postoperative aortic model to obtain a plurality of cross sections;

simulating blood flow in the postoperative aortic model at a predetermined blood flow rate and detecting a pressure intensity difference between a true lumen and a false lumen in each of the cross sections; and evaluating postoperative recovery of the patient based on the pressure intensity difference.

2. The method according to claim 1, wherein the step of evaluating a surgical risk degree of the patient based on the displacement amount comprises:

comparing the displacement amount with a preset displacement amount and evaluating the surgical risk degree of the patient according to a comparison result.

3. The method according to claim 1, subsequent to the step of obtaining the displacement amount of a same vessel node between the preoperative aortic model and the postoperative aortic model with the same vessel node located in the preoperative aortic model and the postoperative aortic model respectively, the method further comprising a step of:

determining, based on a spatial position of the same vessel node in the postoperative aortic model and the displacement amount, a type of a complication that possibly occurs in the patient after surgery.

4. The method according to claim 1, wherein the step of evaluating the postoperative recovery of the patient based on the pressure intensity difference comprises:

obtaining, when determining that there is a cross section with the pressure intensity difference of zero, a position of the cross section in the postoperative aortic model; and evaluating the postoperative recovery of the patient based on the position of the cross section.

5. The method according to claim 1, wherein the step of detecting a pressure intensity difference data between a true lumen and a false lumen in each of the cross sections comprises:

detecting multiple sets of pressure intensity difference data between the true lumen and the false lumen in each of the cross sections; and determining, as the pressure intensity difference, an average value of the multiple sets of pressure intensity difference data.

6. An apparatus for evaluating an aortic dissection surgery, comprising:

a preoperative model obtaining unit, configured to obtain a preoperative aortic model of a patient;

a postoperative model obtaining unit, configured to simulate an aortic dissection surgery based on a virtual stent technology and the preoperative aortic model to obtain a postoperative aortic model;

a displacement amount obtaining unit, configured to obtain a displacement amount of a same vessel node between the preoperative aortic model and the postoperative aortic model with the same vessel node located in the preoperative aortic model and the postoperative aortic model respectively; and a first evaluating unit, configured to evaluate a surgical risk degree of the patient based on the displacement amount;

the apparatus further includes: a cross section obtaining unit configured to transect the postoperative aortic model in a direction perpendicular to a centerline of the postoperative aortic model to obtain a plurality of cross sections;

a pressure intensity difference obtaining unit configured to simulate blood flow in the postoperative aortic model at a predetermined blood flow rate and detect a pressure intensity difference between a true lumen and a false lumen in each of the cross sections; and a second evaluating unit configured to evaluate postoperative recovery of the patient based on the pressure intensity difference.

* * * * *